United States Patent [19]

Wissner et al.

[11] Patent Number: 4,827,011

[45] Date of Patent: May 2, 1989

[54] ANTIHYPERTENSIVE PHOSPHATE DERIVATIVES

[75] Inventors: Allan Wissner, Ardsley, N.Y.; Robert E. Schaub, Upper Saddle River, N.J.

[73] Assignee: American Cyanamid Company, Stamford, Conn.

[21] Appl. No.: 679,790

[22] Filed: Dec. 10, 1984

[51] Int. Cl.$^4$ .................. C07F 9/10; A61K 31/685
[52] U.S. Cl. ................................................ 558/169
[58] Field of Search .................. 260/925; 514/78; 558/169

[56] References Cited

U.S. PATENT DOCUMENTS 4,492,659  1/1985  Bosies et al. ................. 260/925

OTHER PUBLICATIONS

Hanahan et al., Biochemical and Biophysical Research Communications, vol. 99, No. 1, 1981, pp. 183–188.
Tence et al., Biochimie, 1981, 63, 723–727.
Tence et al., Biochimica et Biophysica Acta, 755 (1983) 526–530.

Primary Examiner—Anton H. Sutto
Attorney, Agent, or Firm—Robert P. Raymond

[57] ABSTRACT

Antihypertensive phosphate derivatives having the following formula are described:

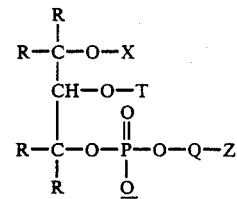

wherein X is a $C_1$–$C_{24}$ branched or straight chain alkyl group; R is selected from the group consisting of hydrogen and $C_1$–$C_4$ alkyl, with the proviso that at least one R group is not hydrogen; T is selected from the group consisting of hydrogen and

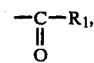

wherein $R_1$ is selected from the group consisting of hydrogen, $C_1$–$C_4$ branched or straight chain alkyl, $C_1$–$C_4$ branched or straight chain alkoxy and $C_1$–$C_4$ branched or straight chain alkylamino; Q is a bivalent radical selected from the group consisting of —($CH_2$)$_p$— and —($CHR^1$)$_p$—, wherein p is an integer from 2 to 12 and the moiety —($CHR^1$)$_p$— represents an alkylene chain which is substituted by one or more $C_1$–$C_{10}$ alkyl groups or phenyl groups; Z is selected from the group consisting of

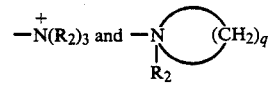

wherein $R_2$ may be chain alkyl and q is an integer from 4 to 7; in either the racemic or in the optically active form.

4 Claims, 4 Drawing Sheets

↓ $N(R_2)_3$ or $R_2-N\underbrace{(CH_2)_q}$, $CH_3CN-CHCl_3$, Δ
   13a     or

25            26

$H_2$, Pd/C, $CH_3COOH$, $CH_3OH$

↓ or

27            28

$(R_1CO)_2O$, $R_1-N=C=O$ or $O(COOR_1)_2$
   16a        16b        16c

↓

29            30

ANTIHYPERTENSIVE PHOSPHATE DERIVATIVES

BACKGROUND OF INVENTION

This invention pertains to novel phosphate derivatives, and to methods of preparation of such compounds. This invention is also concerned with compositions useful in the treatment of hypertension.

It is estimated that approximately fifteen percent (15%) or more of the adult population in the United States is hypertensive, i.e., having blood pressures greater than or equal to about 160/95 mm Hg. Of that population, approximately one-half is unaware of their hypertensive condition. An untreated hypertensive is at great risk of developing disabling or fatal left ventricular failure, myocardial infarction, cerebral hemorrhage or infarction, and renal failure at an early age. Hypertension is generally considered the most important risk factor predisposing to coronary and cerebral atherosclerosis. However, it is believed that effective medical control of hypertension will prevent or forestall all complications associated with hypertension, and will prolong the life of the hypertensive patient.

Drug therapy for hypertension includes use of diuretics, sympathetic depressants (e.g., α-blockers such as reserpine), vasodilators and finally blockers of sympathetic transmission at the neuroeffector junction (e.g., guanethidine or clonidine).

Among the vasodilators currently employed in hypertension therapy are diazoxide and sodium nitroprusside. Side effects of diazoxide therapy include nausea, vomiting, hyperglycemia and tachycardia. Side effects from sodium nitroprusside therapy include nausea, vomiting, agitation, muscular twitching and cutis anserina if blood pressure is reduced too rapidly. Minoxidil is also often used as a vasodilator in hypertension therapy. However, the side effects of minoxidil include sodium and water retension, and hirsutism. Hydralazine, a mild vasodilator, is also employed. Its side effects include headaches, tachycardia, fluid retention, aggravation of angina, gastrointestinal irritation, lupus-like syndrome, drug fever and psychosis.

Acetyl glyceryl ether phosphocholines have been recognized as having potent biological activity in platelet activation, and in vasoconstriction and vasodilation. See, e.g., U.S. Pat. No. 4,329,302, which issued on May 11, 1982 to Hanahan et al. Such phosphocholines have been identified as both a platelet activation factor (PAF) and an antihypertensive polar renomedullary lipid (APRL). See R. L. Wykle et al., FEBS LETTERS, 141: 29-32 (1982); M. L. Blank et al., BIOCHEMICAL AND BIOPHYSICAL RESEARCH COMMUNICATIONS, 90: 1194-1200 (1979). Antihypertensive phosphocholines do not occur as pre-formed components in the body; rather, such phosphocholines are synthesized by certain cells. See J. Benveniste et al., INT. ARCHS. ALLERGY APPL. IMMUNN., 66 (Supp. 1): 121-126 (1981); E. E. Muirhead, HYPERTENSION, 2: 444-464 (1980). APRL has been described as being accountable in great measure for the endocrine-type antihypertensive action exerted by the renal medullary and the renomedullary interstitial cells. M. L. Blank et al., ID.

BRIEF SUMMARY OF THE INVENTION

This invention is concerned with phosphate derivatives of the formula:

wherein X is a $C_1$-$C_{24}$ branched or straight chain alkyl group; R is selected from the group consisting of hydrogen and $C_1$-$C_4$ alkyl, with the proviso that at least one R group is not hydrogen; T is selected from the group consisting of hydrogen and wherein $R_1$ is selected from the group consisting of hydrogen, $C_1$-$C_4$ branched or straight chain alkyl, $C_1$-$C_4$ branched or straight chain alkoxy and $C_1$-$C_4$ branched or straight chain alkylamino; Q is a bivalent radical selected from the group consisting of —$(CH_2)_p$— and —$(CHR^1)_p$—, wherein p is an integer from 2 to 12 and the moiety —$(CHR^1)_p$— represents an alkylene chain which is substituted by one or more $C_1$-$C_{10}$ alkyl groups or phenyl groups; Z is selected from the group consisting of wherein $R_2$ may be the same or different and is selected from the group consisting of hydrogen and $C_1$-$C_4$ branched or straight chain alkyl and q is an integer from 4 to 7. The compounds of this invention can be prepared as separate diastereomers in the racemic and optically active forms.

BRIEF DESCRIPTION OF THE DRAWINGS

Flowsheet A shows synthesis of compounds pertinent to the present invention.

Flowsheet B shows synthesis of compounds pertinent to the present invention.

DETAILED DESCRIPTION OF THE INVENTION

Figure 1A:
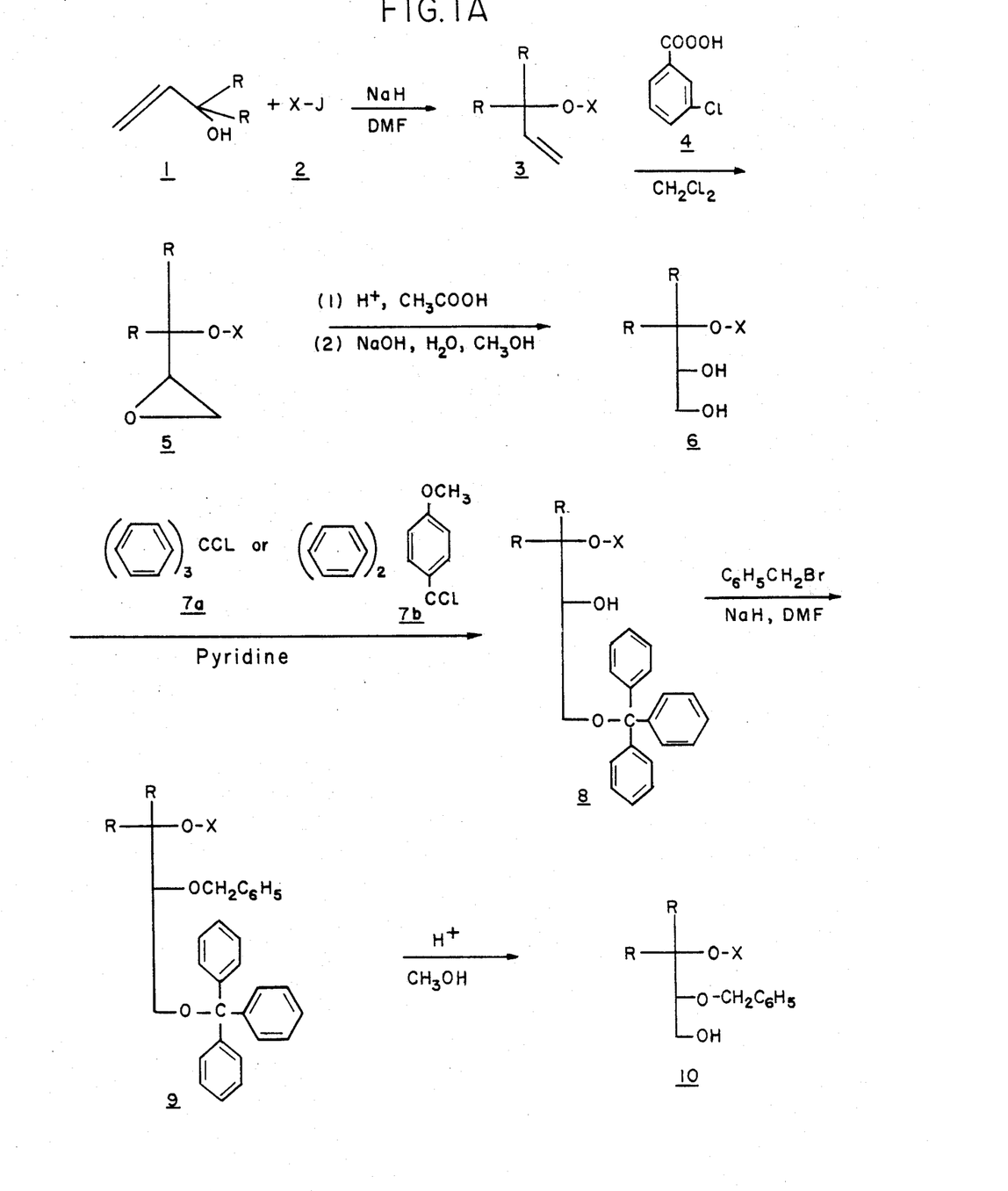
Figure 1B:
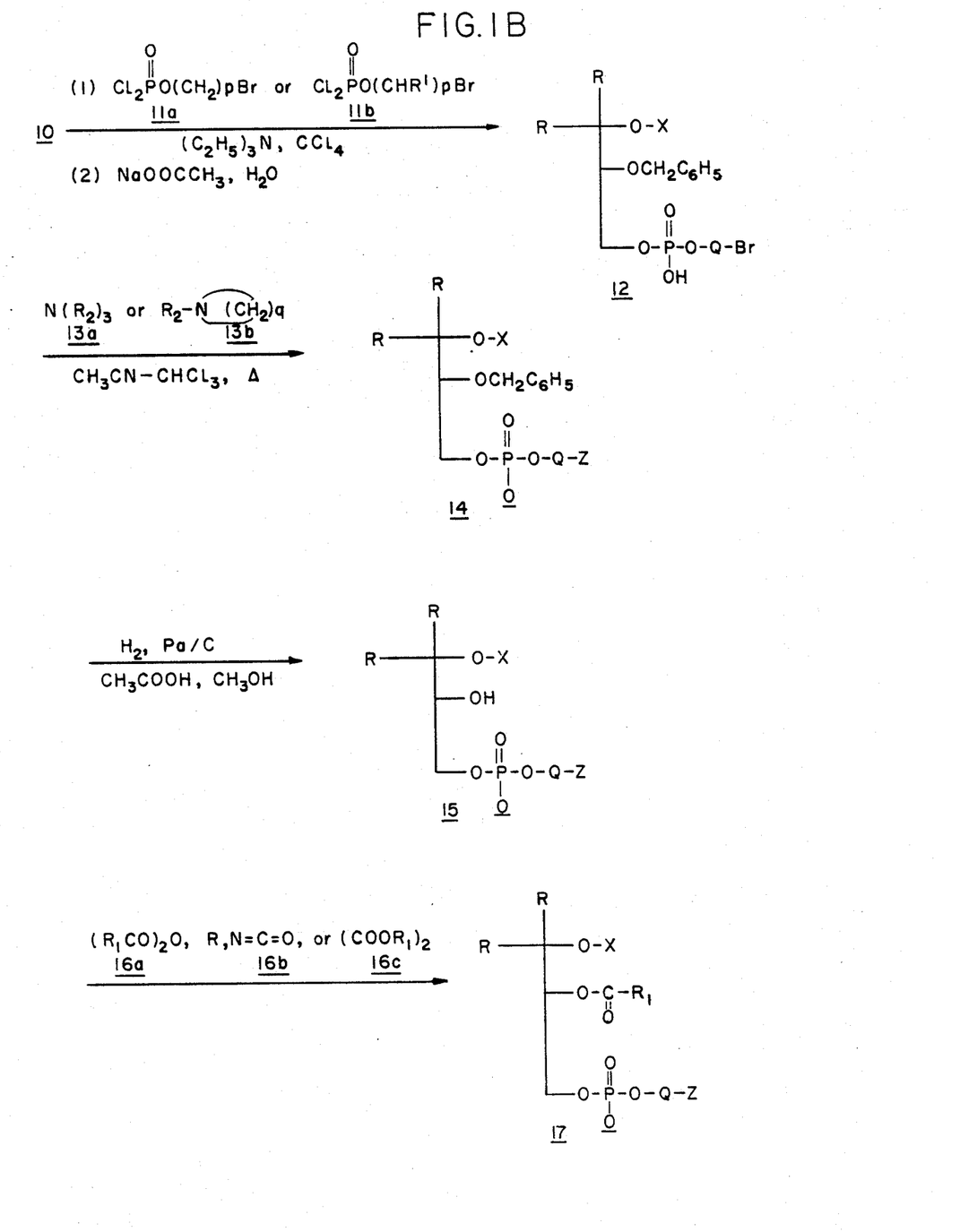
Figure 2A:
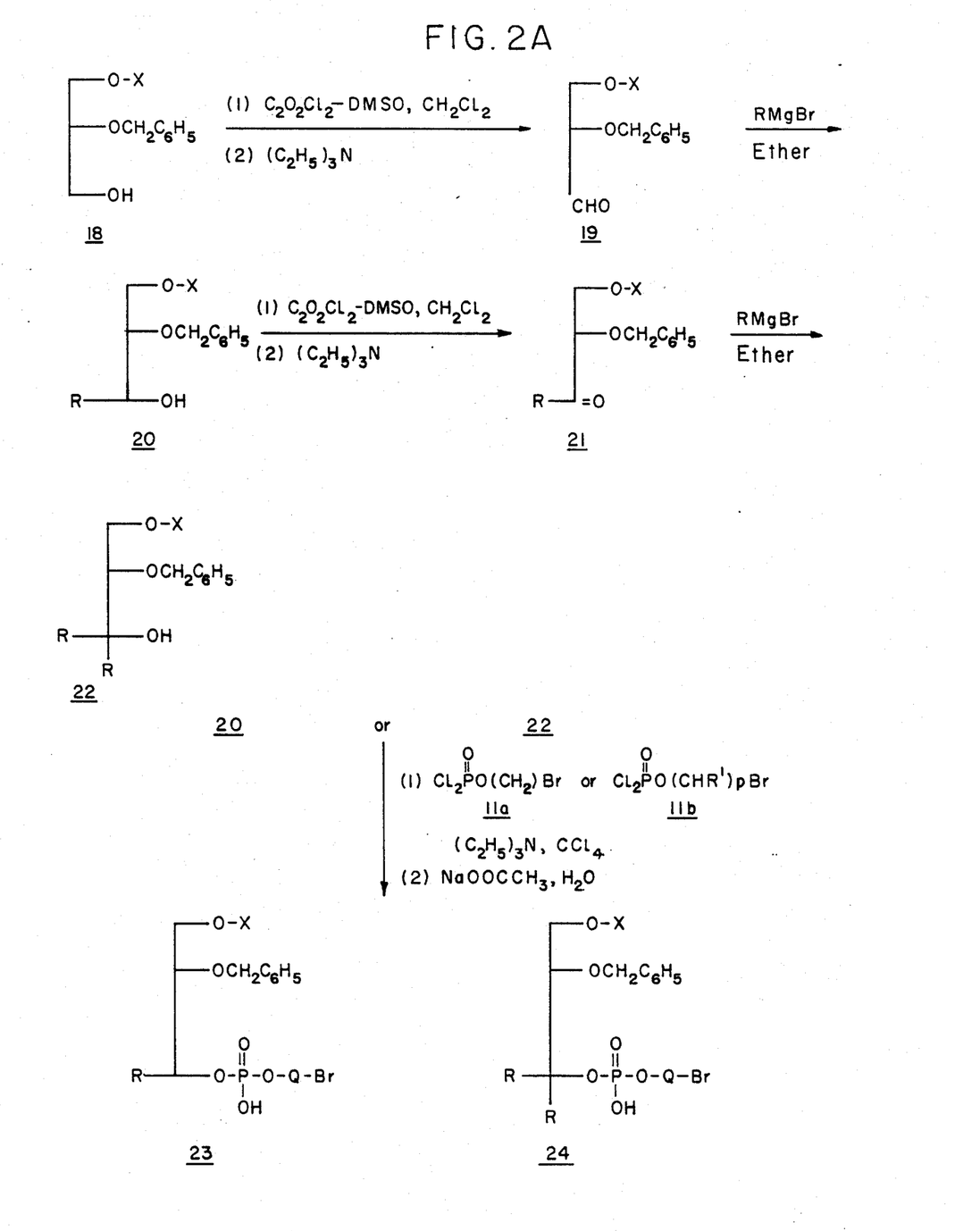
Figure 2B:
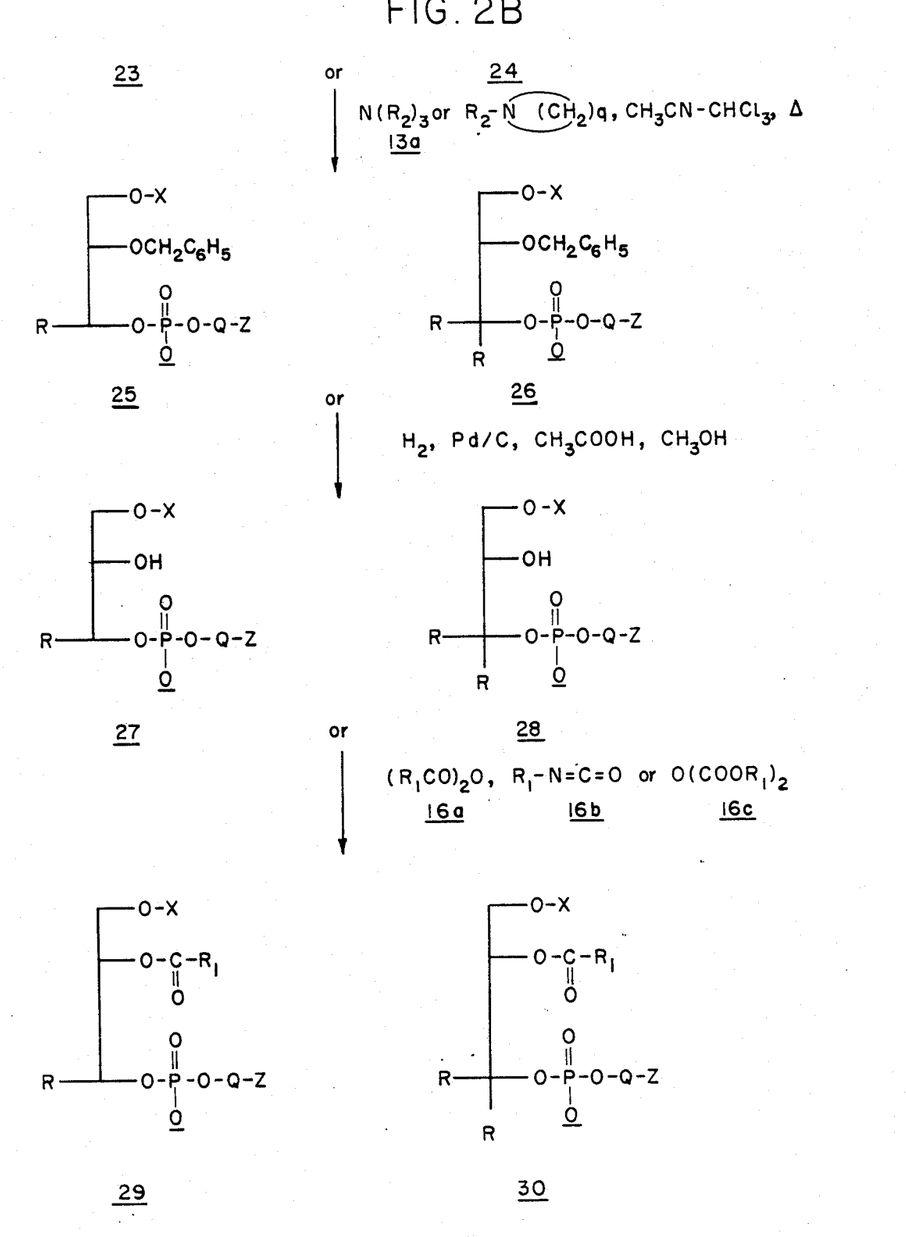

The compounds of this invention represented by structure 17 are prepared as shown in Flowsheet A, wherein R, X, p, Q, Z, q, $R_2$ and $R_1$ are as defined above and J is a halogen atom (Cl, Br, I).

Alkylation of an alcohol 1 with an alkyl halide 2 using sodium hydride in an inert solvent such as dimethylformamide gives the ether 3. Epoxidation of 3 with a peracid 4 such as m-chloroperbenzoic acid gives the oxirane 5. In those cases where the two R groups of 5 are different, 5 is obtained as a mixture of two diastereomers. These can be separated by various chromatographic techniques well known in the art and each individual isomer can be carried through the remaining reactions outlined in Flowsheet A. In some cases it may be desirable to separate the isomers at a later stage in the synthesis. The epoxide ring of 5 is opened by refluxing in acetic acid containing a catalytic amount of a strong acid such as p-toluenesulfonic acid. The resulting mixture of acetates are then hydrolized with aqueous sodium hydroxide in methanol to give diol 6. The diol 6 is reacted with reagent which only functionalizes the primary hydroxyl group; such reagents are p-anisylchlorodiphenylmethane 7b and chlorotriphenylmethane 7a in pyridine or mixed solvent containing pyidine. This provides the monoprotected compound 8 which is converted to the compound 9 by alkylation with benzyl bromide using sodium hydride in an inert solvent. Treatment of 9 with methanol and an acid catalyst such p-toluenesulfonic acid or an acidic ion exchange resin gives the alcohol 10. The reaction of 10 with the phosphorous reagents 11a or 11b in an inert solvent such as carbon tetrachloride with a base such as triethylamine gives, after hydrolysis in a buffer such as aqueous sodium acetate, the phosphate compound 12. The reaction of 12 with amines 13a or 13b in a refluxing inert solvent or in a bomb at elevated temperature affords compound 14. The benzyl protecting group of 14 is removed by hydrogenolysis to give the alcohol 15.

The compounds represented by the formula 15 can be converted to compounds 17 of this invention wherein $R_1$ is an alkyl group by the reaction of 15 with an anhydride 16a in the presence of a base catalyst such as triethylamine in an inert solvent such as chloroform.

The compounds represented by the formula 15 can be converted to compounds 17 of this invention wherein $R_1$ is hydrogen by the reaction of 15 with about 97% formic acid at room temperature for about 3 to 7 days.

The compounds represented by the formula 15 can be converted to compounds 17 of this invention wherein $R_1$ is a $C_1$-$C_4$ alkylamino group by treatment of 15 with an isocyanate 16b in an inert solvent such as toluene at about 25°-100° C. for about 1-7 days.

The compounds represented by the formula 15 can be converted to compounds 17 of this invention wherein $R_1$ is a $C_1$-$C_4$ alkoxy group by the reaction of 15 with a pyrocarbonate 16c in the absence of solvents at elevated temperature (about 50°-150° C.).

The compounds of this invention represented by structures 29 and 30 are prepared as outlined in Flowsheet B, wherein R, X, p, q, Q, Z, $R_2$ and $R_1$ are as defined above.

One method for the preparation of compounds of the structure 18 is given in Flowsheet A (10, R=H); other methods are described in detail in a copending application for U.S. patent Ser. No. 457,097, filed Jan. 10, 1983, and patented Feb. 3, 1987 under U.S. Pat. No. 4,640,913, which patent is incorporated herein by reference. Representative of such methods are Examples 24-28 herein which correspond to Examples 25-29 of Ser. No. 457,097. Representative of the compounds capable of being used in the present invention are shown in Table III following Exmaple 28 herein which corresponds to Table III of Ser. No. 457,097.

Oxidation of 18 with oxalyl chloride-dimethyl sulfoxide at low temperature in an inert solvent gives, after treatment with an amine base such as triethylamine, the aldehyde 19. The reaction of 19 with an alkyl Grignard reagent in ether gives alcohol 20 which can be oxidized as before to give the ketone 21. Introduction of a second alkyl group is again performed with a Grignard reagent giving 22. For compound 20, and in those cases where the two R groups of 22 are different, two diasteromers are produced. These can be separated using various chromatographic techniques well known in the art. Each isomer of 20 and 22 can then be carried through the remaining reactions of Flowsheet B.

The reaction of 20 or 22 with the phosphorous reagents 11a or 11b in an inert solvent such as carbon tetrachloride with a base such as triethylamine gives after hydrolysis in a buffer such as aqueous sodium acetate, the phosphate compounds 23 or 24. The reaction of 23 or 24 with amines 13a or 13b in a refluxing inert solvent or in a bomb at elevated temperature affords compounds 25 or 26. The benzyl protecting groups of 25 or 26 are removed by hydrogenolysis to give the alcohols 27 or 28, respectively. Representative alkyl amines capable of being used in the present invention are shown in Table IV following Example 28 herein which corresponds to Table VIII of Ser. No. 457,097.

The compounds represented by the formula 27 or 28 be converted to compounds 29 or 30 of this invention wherein $R_1$ is an alkyl group by the reaction of 27 or 28 with an anhydride 16a in the presence of a base catalyst such as triethylamine in an inert solvent such as chloroform.

The compounds represented by the formula 27 or 28 can be converted to compounds 29 or 30 of this invention wherein $R_1$ is a $C_1$-$C_4$ alkoxy group by the reaction of 27 or 28 with a pyrocarbonate 16c in the absence of solvent at elevated temperature (about 50°-150° C.).

The compounds represented by the formula 27 or 28 can be converted to compounds 29 or 30 of this invention wherein $R_1$ is hydrogen by the reaction of 27 or 28 with about 97% formic acid at room temperature for about 3 to 7 days.

The compounds represented by the formula 27 or 28 be converted to compounds 29 or 30 of this invention wherein $R_1$ is a $C_1$-$C_4$ alkylamino group by treatment of 27 or 28 with an isocyanate 16b in an inert solvent such as toluene at about 25°-100° C. for about 1-7 days.

Since compound 18 is available in either the optically active R or S forms (see U.S. Pat. No. 4,640,913), or in the optically inactive racemic form, the compounds of this invention represented by the formula 29 and 30 can be prepared in the corresponding optically active R and S configurations or in the optically inactive racemic form by choosing the proper starting material [E. Baer, BIOCHEMICAL PREP., 2: 31 (1952); M. E. Jung and T. J. Shaw, J. AMER. CHEM. SOC., 102: 6304 (1980)].

By following the methods outlined hereinabove in Flowsheet B, it is also possible to convert compounds of structure 10 to other compounds of this invention represented by structures 31 and 32.

10

Not only can the compounds of this invention represented by structure 17 be obtained, as described above, as the separated diastereomers when the two R groups are different, but each diastereomer can be obtained in optically active form providing the starting alcohol 1 is resolved into its component R and S enantiomers. This can be accomplished as described in detail by A. W. Ingersoll, "The Resolution of Alcohols", ORG. REACT., chapter 9 (1944).

The methods for the preparation of the phosphorous reagents 11a and 11b, used to prepare the compounds of this invention, are described in detail in U.S. Pat. No. 4,640,913 and in the following references: E. Baer and N. Z. Stanacey, J. BIOL. CHEM., 24, 3754 (1965); A. Eberhard and F. H. Westheimer, J. AMER. CHEM. SOC., 37, 253 (1965). By using such procedures the bromo alcohols of Table I are converted to the indicated phosphorodichlorodates.

TABLE I

| Bromo Alcohol | Phosphorodichlorodate |
| --- | --- |
| 2-bromoethanol | 2-bromoethyl phosphorodichlorodate |
| 3-bromopropanol | 3-bromopropyl phosphorodichlorodate |
| 2-bromopropanol | 2-bromopropyl phosphorodichlorodate |
| 2-bromo-1-methylethanol | 2-bromo-1-methylethyl phosphorodichlorodate |
| 4-bromobutanol | 4-bromobutyl phosphorodichlorodate |
| 5-bromopentanol | 5-bromopentyl phosphorodichlorodate |
| 3-bromo-3-methylpropanol | 3-bromo-3-methylpropyl phosphorodichlorodate |
| 3-bromo-2-methylpropanol | 3-bromo-3-methylpropyl phosphorodichlorodate |
| 3-bromo-1-methylpropanol | 3-bromo-1-methylpropyl phosphorodichlorodate |
| 2-bromo-2-phenylethanol | 2-bromo-2-phenylethyl phosphorodichlorodate |
| 3-bromo-2-phenylpropanol | 3-bromo-2-phenylpropyl phosphorodichlorodate |

The compounds of the present invention are active as hypotensive agents as evidenced by their activity in the following test, the results of which are shown in Table II.

Under ether anesthesia, Weeks type cannulas (Peterson Technics) were surgically implanted in the abdominal aorta and vena cava of spontaneously hypertensive rats (Taconic Farms, Germantown, N.Y.) and passed subcutaneously to the back of the neck where they were exteriorized. The cannulas were filled with saline, plugged and the rats returned to single cages where they were allowed food and water ad libitum.

At least three days following implantation of the cannulas, the rats were weighed and placed in Broome style restraining cages. The plug was removed from the aortic catheter which was connected to an arterial pressure transducer (Statham P23ID) using PE 100 polyethylene tubing and a stepdown connector fabricated from stainless steel hypodermic tubing. Mean arterial blood pressure was obtained by electrical damping of the pulse pressure channel. Heart rate was obtained from a tachograph triggered by the pulse pressure channel. All parameters were monitored on a Grass physiological recorder (Model 7).

The plug was removed from the vena cava catheter and a PE 20 polyethylene tubing extension was added using a piece of stainless steel hypodermic tubing. The other end was terminated with a 27G needle and one ml syringe.

All drugs were dissolved in saline or a mixture of ethanol and saline (25:75 V:V) such that the volume injected intravenously was 0.1 ml/100 g body weight. All drugs were flushed in with 0.2 ml saline. Blood pressure was continually monitored both before and after introduction of the test compound.

TABLE II

| Compound | Dose (μg/kg) | No. of Rats | Peak Δ Mean Arterial Blood Pressure (mm, Hg) |
| --- | --- | --- | --- |
| 7-(Acetyloxy)-4-hydroxy-N,N,N,8-tetramethyl-3,5,-9-trioxa-4-phosphapentacosan-1-aminium, 4-oxide, hydroxide, inner salt | 1 | 4 | −9.4 |
| | 3 | 4 | −22.7 |
| | 10 | 4 | −56.8 |
| | 30 | 4 | −86.9 |
| 7-(Acetyloxy)-4-hydroxy-N,N,N,6-tetramethyl-3,5,9-trioxa-4-phosphapentacosan-1-aminium, 4-oxide, hydroxide, inner salt | 30 | 4 | −28.9 |
| | 100 | 4 | −60.2 |
| | 300 | 4 | −97.9 |
| | 1000 | 4 | −109.3 |
| 7-(Acetyloxy)-4-hydroxy-N,N,N,8,8-pentamethyl-3,5,9-trioxa-4-phosphapentacosan-1-aminium, 4-oxide, hydroxide, inner salt | 100 | 4 | −11.2 |
| | 300 | 4 | −24.2 |
| | 1000 | 4 | −56.5 |

When the compounds are employed for the above utility, they may be combined with one or more pharmaceutically acceptable carriers, e.g., solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 0.05% up to about 90% of the active ingredient in combination with the carrier, more usually between about 5% and 60% by weight.

The effect dosage of active ingredient employed may vary depending on the particular compound employed, the mode of administration and the severity of the condition being treated. However, in general, satisfactory results are obtained when the compounds of the invention are administered at a daily dosage of from about 0.005 mg to about 100 mg/kg of animal body weight, preferably given in divided doses two to four times a day, or in sustained release form. For most large mammals the total daily dosage is from about 500 μg to about 5,000 mg preferably from about 350 μg to 3,500 mg. Dosage forms suitable for internal use comprise from about 25 μg to 50 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are solid composition, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropyl-cellulose. Dispersions can also be prepared in glycerol, liquid polyethylene glycols, and mixtures thereof in oils. Under ordinary conditions of storage and use, these preparations should contain a preservative to prevent the growth of microorganisms.

The pharmaceutical forms suitable for injection use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

In addition to the above utility, some of the compounds of this invention (such as 15 of Flowsheet A and 32 of Flowsheet B) are useful for the preparation of other compounds of this invention.

The invention will be more fully described in conjunction with the following specific examples which are not to be construed as limiting the scope of the invention. In addition, other applicable procedures are described in the aforementioned copending application, Ser. No. 457,097, filed Jan. 10, 1983 and in the prior art.

EXAMPLE 1

1-[(1-Methyl-2-propenyl)oxy]hexadecane

To a suspension of 10.57 g of hexane washed 50% sodium hydride in 150 ml of dimethylformamide, under argon, was added with stirring a solution fo 16.58 g of 3-butene-2-ol in 100 ml of dimethylformamide, dropwise over 30 minutes. After gas evolution ceased 76 g of n-hexadecyl tosylate was added followed by 70 ml of dimethylformamide. The mixture was stirred overnight then poured into water and extracted with petroleum ether:ether. The extract was dried, the solvent removed and the residue distilled via Kugelrohr (180°–185° C., 0.35 mm), giving 50.9 g of the desired compound as a colorless oil.

EXAMPLE 2

1-[(1,1-Dimethyl-2-propenyl)oxy]hexadecane

To a suspension of 23.59 g of hexane washed 50% sodium hydride in 300 ml of dimethylformamide under argon, was added with stirring 55.38 g of 1,1-dimethyl-2-propenol, dropwise over 1 hour. The mixture was cooled to 0° C., 150 g of n-hexadecyl tosylate and 50 ml of tetrahydrofuran were added and this mixture was stirred overnight at room temperature. Water was added and the mixture was extracted with ether. The ether extract was dried and the solvent removed. One half of the residue as chromatographed by HPLC [hexane:ether (90:1)], giving 37.8 g of the desired compound as a colorless liquid.

EXAMPLE 3

[1-(Hexadecyloxy)ethyl]oxirane

A mixture of 46.9 g of 1-[(1-methyl-2-propenyl)oxy]-hexadecane, 32.19 g of m-chloroperbenzoic acid and 300 ml of methylene chloride was stirred overnight and then filtered. The filtrate was evaporated and the residue dissolved in petroleum ether:ether and washed with saturated aqueous sodium bicarbonate. The solution was dried, the solvent removed and the residue chromatographed via HPLC (two columns), eluting first with hexane to remove higher Rf impurities and then with 10% ether in hexane to elute the product, giving the desired compound as a clear oil.

EXAMPLE 4

[1-(Hexadecyloxy)-1-methylethyl]oxirane

A mixture of 36.5g of 1-[(1,1-dimethyl-2-propenyl)oxy]hexadecane, 23.92 g of m-chloroperbenzoic acid and 225 ml of methylene chloride was stirred overnight. A 7 g portion of m-chloroperbenzoic acid was added, then the mixture was stored in a chill room for 56 hours. This mixture was filtered. The filtrate was washed with dilute aqueous sodium bisulfite, then saturated aqueous sodium bicarbonate, dried and the solvent removed, giving 36 g of the desired compound.

EXAMPLE 5

3-(Hexadecyloxy)-1,2-butanediol

A mixture of 30 g of [1-(hexadecyloxy)ethyl]oxirane, 0.2 g of p-toluenesulfonic acid and 200 ml of glacial acetic acid was refluxed for 4.5 hours, then the acetic acid was removed. Toluene was added and removed. The residue was dissolved in 225 ml of methanol and 13.44 g of sodium hydroxide in 14 ml of water was added. This mixture was stirred ½ hour, the solvent removed and the residue extracted twice with ether. The ether extracts were combined, washed with brine, dried and the solvent removed. The resulting oil was diluted via a Kugelrohr (200° C., 0.5 mm), giving 28.87 g of the desired compound as a white sticky solid.

EXAMPLE 6

3-(Hexadecyloxy)-3-methyl-1,2-butanediol

A mixture of 35 g of [1-(hexadecyloxy)-1-methylethyl]oxirane, 30.07 g of potassium hydroxide, 70 ml of water and 450 ml of dimethyl sulfoxide was stirred at 110° C. for 8 hours, then cooled, poured into water and extracted with ether. The ether extract was dried and the solvent removed. The residue was chromatographed via HPLC, eluting with hexane:ethyl acetate (4:1). The lower Rf component was the desired compound, giving 18.2 g of an oil.

EXAMPLE 7

3-(Hexadecyloxy)-1-(triphenylmethoxy)-2-butanol

A mixture of 27.5 g of 3-(hexadecyloxy)-1,2-butanediol, 34.79 g of trityl chloride and 125 ml of pyridine was allowed to stand 48 hours and then poured into water. A mixture of ether-petroleum ether was added, followed by dilute hydrochloric acid. The organic layer was separated, washed with dilute hydrochloric acid, then brine, dried and the solvent removed. The residue was mixed with petroleum ether and allowed to stand several days. After filtration, the filtrate was evaporated, giving 46.6 g of the desired compound as an oil, which was used in Example 9 without further purification.

EXAMPLE 8

3-(Hexadecyloxy)-1-[(4-methoxyphenyl)diphenylmethoxy]-3-methyl-2-butanol

A mixture of 17.5 g of 3-(hexadecyloxy)-3-methyl-1,2-butanediol, 17.87 g of p-methoxy trityl chloride, 10 ml of pyridine and 40 ml of tetrahydrofuran was allowed to stand for 3 hours, then the tetrahydrofuran was removed. Ether was added, the mixture washed with water, dried and the sovlent removed, giving the desired compound as an oil which was used without further purification in Example 10.

EXAMPLE 9

3-(Hexadecyloxy)-2-(phenylmethoxy)-1-butanol

To a suspension of 5.01 g of 50% sodium hydride in 100 ml of dimethylformamide containing 15.79 g of benzyl bromide at 0° C., was added 46 g of 3-(hexadecyloxy)-1-(triphenylmethoxy)-2-butanol in 50 ml of dimethylformamide. This mixture was stirred overnight at room temperature then poured into water and extracted with petroleum ether. The organic extract was dried and the solvent removed. The residue was dissolved in a mixture of 190 ml of methanol and 100 ml of tetrahydrofuran, then 400 mg of p-toluenesulfonic acid was added. This mixture was allowed to stand overnight, then the solvent was removed. The residue was dissolved in petroleum ether, washed wtih saturated aqueous sodium bicarbonate, dried and the solvent removed, giving and oil. This oil was purified by HPLC using the system hexane:ethyl acetate (9:1), giving 21.84 g of the desired compound as an oil.

EXAMPLE 10

3-(Hexadecyloxy)3-methyl-2-(phenylmethoxy)-1-butanol

To a suspension of 3.28 g of 50% sodium hydride in 40 ml of dimethylformamide containing 13.49 g of benzyl bromide was added dropwise a solution of 31.8 g of 3-(hexadecyloxy)-1-[(4-methoxyphenyl)diphenylmethoxy]-3-methyl-2-butanol in 50 ml of dimethylformamide over 45 minutes. The mixture was stirred overnight, then water was added and the mixture extracted with ether. The ether extract was dried and the solvent removed. The residue was stirred with 125 ml of methanol, 25 ml of tetrahydrofuran and 10 g of a strongly acidic ion exchange resin for 1.5 hours with warming, then filtered and the solvent removed. The residue was purified by HPLC, using hexane:ether (9:1), giving 12.14 g of the desired compound as a light yellow oil.

EXAMPLE 11

3-(Hexadecyloxy)-2-(phenylmethoxy)-propanol

A stirred solution of 9.36 g of oxalyl chloride in 130 ml of methylene chloride, under an argon atmosphere was cooled to −70° C. To this was added dropwise 11.53 g of dried dimethyl sulfoxide at a rate to maintain the temperature at −65° to −70° C. After stirring 5 minutes a solution of 10 g of 3-(hexadecyloxy)-2-(phenylmethoxy)-1-butanol in 60 ml of methylene chloride was added dropwise at a fast rate. The pasty mixture was allowed to warm to −10° C. over 20 minutes providing a solution. This solution was recooled to −50° C. and 16.17 g of triethylamine was added dropwise. The reaction mixture was allowed to warm to room temperature and was then poured into 100 ml of water. The organic phase was separated, washed successively with 0.5N hydrochloric acid, saturated aqueous sodium bicarbonate and brine, dried and the solvents removed giving an oil. This oil was dissolved in petroleum ether, washed with water and taken to dryness, giving 10 g of the desired compound as a yellow oil.

EXAMPLE 12

4-(Hexadecyloxy)-3-(phenylmethoxy)-2-butanol

To a solution of 10 g of 3-(hexadecyloxy)-2-(phenylmethoxy)-propanal in 120 ml of dry tetrahydrofuran, under argon, at 5° C., was added dropwise 16.4 ml of 3M methyl magnesium bromide in ether at a rate to maintain the temperature below 8° C. The mixture was stirred at 5° C. for 15 minutes, then at room temperature for 3 hours, recooled to 5° C. and 50 ml of 1N hydrochloric acid was added dropwise at a rate to maintain the temperature below 10° C. The organic phase was separated and the aqueous phase extracted with ether. The ether extract was combined with the organic phase, washed with saturated aqueous sodium bicarbonate, then saturated brine, dried and taken to dryness. The residue was dissolved in petroleum ether, washed with saline, dried and taken to dryness. The residue was purified by HPLC using ether:hexane (1:5), giving 6.16 g of the desired compound as a pale yellow oil.

EXAMPLE 13

2-Bromoethyl 3-(hexadecyloxy)-2-(phenylmethoxy) phosphoric acid, butyl ester A mixture of 20 g of 3-(hexadecyloxy)-2-(phenylmethoxy)-1-butanol, 20.12 g of 2-bromoethyl phosphorodichlorodate, 8.42 g of triethylamine and 230 ml of carbon tetrachloride was stirred for 3 hours, then filtered through diatomaceous earth and the solvent removed. The residue was added to a mixture of 580 ml of 0.5M aqueous sodium acetate and 580 ml of tetrahydrofuran, stirred overnight, then the tetrahydrofuran was removed. The remainder was acidified wtih dilute hydrochloric acid and extracted with ether. The ether extract was washed with brine, dried and the solvent removed, giving the desired compound as a yellow oil which was used in Example 14 without further purification.

EXAMPLE 14

4-Hydroxy-N,N,N,8-tetramethyl-7-(phenylmethoxy)-3,5,9-trioxa-4-phosphapentacosan-1-aluminum, 4-oxide, hydroxide, inner salt A mixture of 28 g of 2-bromoethyl 3-(hexadecyloxy)-2-(phenylmethoxy)phosphoric acid, butyl ester, 375 ml of 40% aqueous trimethylamine and 650 ml of chloroform:2-propanol:dimethylformamide (3:5:5) was heated at 55°–60° C. for 5 hours. The volatile solvents were removed, 8 g of silver carbonate were added, this mixture stirred for 1.5 hours, filtered through diatomaceous earth and the solvent removed. The residue was chromatographed on 800 g of silica gel eluting with chloroform, then chloroform:methanol (9:1) to remove higher Rf impurities and then with chloroform:methanol (1:1) to elute the product, giving 10.42 g of the desired compound as a white foam.

EXAMPLE 15

4-Hydroxy-N,N,N,8,8-pentamethyl-7-(phenylmethoxy)-3,5,9-trioxa-4-phosphapentacosan-1-aminium, 4-oxide, hydroxide, inner salt A mixture of 11 g of 3-(hexadecyloxy)-3-methyl-2-(phenylmethoxy)-1-butanol, 9.18 g of 2-bromoethyl phosporodichlorodate, 3.84 of triethylamine and 125 ml of chloroform was stirred for 1.5 hours, filtered and the solvent removed. The residue was added to a mixture of 300 ml of 0.5M aqueous sodium acetate and 300 ml of tetrahydrofuran, stirred for 2 hours, then the tetrahydrofuran was removed under reduced pressure. The aqueous hydrochloric acid and extracted with ether. The ether extract was washed with water, dried and evaporated. The residue was added to a mixture of 200 ml of acetonitrile, 180 ml of chloroform and 100 g of trimethylamine and refluxed for 3 hours. The solvents were removed and the residue stirred in a mixture of 2 g of silver carbonate, 8 g of a strongly acidic ion exchange resin and 100 ml of methanol for ½ hour, then filtered and the solvent removed. The residue was chromatographed on 400 g of silica gel, eluting first with chloroform:methanol (9:1) to remove higher Rf impurities and then with chloroform:methanol:water (70:30:25) to elute the product, giving 5.4 g of the desired compound as a solid.

EXAMPLE 16

2-Bromoethyl 3-(hexadecyloxy)-1-methyl-2-(phenylmethoxy) phosphoric acid, propyl ester To solution of 4.7 g of 2-bromoethyl phosphorodichlorodate in 100 ml of carbon tetrachloride, cooled in an ice bath under argon, was added dropwise 7.9 g of triethylamine, followed by the dropwise addition of a solution of 4-(hexadecyloxy)-3-(phenylmethoxy)-2-butanol in 5 ml of carbon tetrachloride. This mixture was stirred at room temperature for 48 hours, then diluted with 200 ml of toluene, filtered through diatomaceous earth and the solvents removed. The residue was added to a mixture of 80 ml of tetrahydrofuran and 80 ml of 0.5M aqueous sodium acetate under argon and stirred for 6 hours. The tetrahydrofuran was removed under reduced pressure. The aqueous remainder was acidified with 0.5N hydrochloric acid and extracted twice with ether. The ether extracts were combined, washed with saturated brine, dried over magnesium sulfate and activated charcoal and then taken to dryness giving a viscous yellow oil. This oil was chromatographed on a column of magnesium silicate, developing first with chloroform and then with 10% methanol in chloroform giving 5.11 g of the desired compound as an oil.

EXAMPLE 17

4-Hydroxy-N,N,N,6-tetramethyl-7-(phenylmethoxy)-3,5,9-trioxa-4-phosphapentacosan-1-aminium, 4-oxide, hydroxide, inner salt A solution of 5 g of 2-bromoethyl 3-(hexadecyloxy)-1-methyl-2-(phenylmethoxy)phosphoric acid, propyl ester in 100 ml of acetonitrile, 90 ml of chloroform and 50 ml of trimethylamine was stirred at reflux for 16 hours. The solvents were removed in vacuo, the residue dissolved in 50 ml of methanol, 1.25 g of silver carbonate added and this mixture stirred or 3 hours. This mixture was filtered through diatomaceous earth, washed with methanol and the mother liquor taken to dryness, leaving a foam. The addition of 150 ml of ether caused the foam to solidify. This mixture was refrigerated for 48 hours, then cooled at −20° C. The solid was collected, washed with ether and dried, giving 3.59 g of the desired compound.

EXAMPLE 18

4,7-Dihydroxy-N,N,N,8-tetramethyl-3,5,9-trioxa-4-phosphopentacosan-1-aminium, 4-oxide, hydroxide, inner salt A mixture of 10 g of 4-hydroxy-N,N,N,8-tetramethyl-7-(phenylmethoxy)-3,5,9-trioxa-4-phosphapentacosan-1-aminium, 4-oxide, hydroxide, inner salt, 1 g of 5% palladium on carbon, 65 ml of glacial acetic acid and 65 ml of methanol was hydrogenated in a Parr aparatus for 20 hours. The mixture was filtered, the solvent removed and the residue stirred with moist ether for 2 hours. The solid was collected, giving 7.4 g of the desired compound.

EXAMPLE 19

4,7-Dihydroxy-N,N,N,8,8-pentamethyl-3,5,9-trioxa-4-phosphapentacosan-1-aminium, 4-oxide, hydroxide, inner salt A mixture 5 g of 4-hydroxy-N,N,N,8,8-pentamethyl-7-(phenylmethoxy)-3,5,9-trioxa-4-phosphapentacosan-1-aminium, 4-oxide, hydroxide, inner salt, 0.5 g of 5% palladium on carbon, 30 ml of glacial acetic acid and 30 ml of methanol was hydrogenated in a Parr apparatus for 3 hours. The mixture was filtered, the solvent removed, ether added and the solid collected, giving 3.93 g of the desired compound as a white powder.

EXAMPLE 20

4,7-Dihydroxy-N,N,N,6-tetramethyl-3,5,9-trioxa-4-phosphapentacosan-1-aminium, 4-oxide, hydroxide, inner salt A mixture of 3.5 g of 4-hydroxy-N,N,N,6-tetramethyl-7-(phenylmethoxy)-3,5,9-trioxa-4-phosphapentacosan-1-aminium, 4-oxide, hydroxide, inner salt, 600 mg of 5% palladium on carbon, 35 ml of glacial acetic acid and 35 ml of methanol was hydrogenated on a Parr apparatus for 20 hours. The mixture was filtered through diatomaceous earth, the mother liquor taken to dryness and evaporated three times with toluene. The syrupy residue was triturated with 60 ml of ether for 1 hour and then refrigerated at 0° C. overnight. The solid was collected, washed with cold ether and dried in vacuo, giving 2.69 g of the desired compound as a white solid.

EXAMPLE 21

7-(Acetyloxy)-4-hydroxy-N,N,N,8-tetramethyl-3,5,9-trioxa-4-phosphapentacosan-1-aminium, 4-oxide, hydroxide, inner salt A mixture of 6.4 g of 4,7-dihydroxy-N,N,N,8-tetramethyl-3,5,9-trioxa-4-phosphapentacosan-1-aminium, 4-oxide, hydroxide, inner salt, 32.95 g of acetic anhydride, 13.07 g of triethylamine and 325 ml of chloroform was refluxed for 2.5 hours. The solvent and excess anhydride were removed at reduced pressure. The residue was chromatographed on silica gel eluting with chloroform:methanol (7:3), then chloroform:methanol (1:1) to remove higher Rf impurities and then with chloroform:methanol:water (70:30:5) to elute the product. The solvent was removed and the residue dissolved in a minimum of chloroform, precipitated with ether and dried in vacuo, giving 4.6 g of the desired product.

EXAMPLE 22

7-(Acetyloxy)-4-hydroxy-N,N,N,8,8-pentamethyl-3,5,9-trioxa-4-phosphapentacosan-1-aminium, 4-oxide, hydroxide, inner salt A mixture of 3 g of 4,7-dihydroxy-N,N,N,8,8-pentamethyl-3,5,9-trioxa-4-phosphapentacosan-1-aminium, 4-oxide, hydroxide, inner salt, 15.02 g of acetic anhydride, 5.96 g of triethylamine and 200 ml of chloroform was refluxed for 15 hours. The solvent and excess anhydride were removed and the remainder chromatographed on silica gel, eluting first with chloroform:methanol (8:2) to remove higher Rf impurities, then eluting the product with chloroform:methanol:water (70:30:2.5). The solvent was removed, the product precipitated with ether and collected, giving 1.0 g of the desired product.

EXAMPLE 23

7-(Acetyloxy)-4-hydroxy-N,N,N,6-tetramethyl-3,5,9-trioxa-4-phosphapentacosan-1-aminium, 4-oxide, hydroxide, inner salt A mixture of 2 g of 4,7-dihydroxy-N,N,N,6-tetramethyl-3,5,9-trioxa-4-phosphapentacosan-1-aminium, 4-oxide, hydroxide, inner salt, 10.3 g of acetic anhydride, 4.08 g of triethylamine and 100 ml of chloroform was stirred at refluxed or 3.5 hours. The solvents were removed under reduced pressure and the residue evaporated three times with toluene, leaving a glass. This glass was chromatographed on silica gel, eluting with 500 ml of chloroform, then 250 ml of chloroform:methanol (70:30), then 250 ml of chloroform:methanol (50:50) to remove mobile impurities, then eluting the product with chloroform:methanol:water (65:35:6). The solvent was evaporated and the residue evaporated twice from toluene. The residue was dissolved in chloroform, filtered through diatomaceous earth and taken to dryness. This residue was triturated with ether and refrigerated at 0° C. for 48 hours. The solid was collected, washed with cold ether and dried, giving 1.13 g of the desired product as a white solid, mp 75°–80° C.

Compounds of the structure 18 in Flowchart B may also be prepared by following the procedures of Examples 24–28.

EXAMPLE 24

2-Phenyl-m-dioxan-5-ol

A mixture of about 184 g of glycerol, about 212.03 g of benzaldehyde and about 3.6 g of p-toluenesulfonic acid was refluxed for about 5 hours, using a Dean-Stark trap. The mixture was then cooled at about 0° C. for about 17 hours and the solid collected and dissolved in about 1200 ml of warm toluene containing about one gram of sodium methoxide. This solution was washed with about 600 ml of dilute (about 1%) dibasic sodium phosphate and dried. Dilution with petroleum ether gave a solid which was recrystallized from toluene-petroleum ether, giving about 76 g of the desired title compound as a white solid.

EXAMPLE 25

5-(Benzyloxy)-2-phenyl-m-dioxane

To a suspension of about 19.63 g of about 50% sodium hydride in about 450 ml of dimethylformamide was added, portionwise, over about 15 minutes about 67 g of 2-phenyl-m-dioxan-5-ol. After stirring about 20 minutes, the mixture was cooled in ice and about 69.95 g of benzyl bromide was added dropwise over about 20 minutes. The mixture was stirred at room temperature overnight, water was added and the solid collected. This solid was dissolved in hot toluene, dried, filtered and diluted with an equal volume of petroleum ether. After standing about 4 hours at about 0° C. the solid was collected, giving about 90.5 g of the desired title compound.

EXAMPLE 26

2-(Benzyloxy)-1,3-propanediol

A mixture of about 338 g of 5-(benzyloxy)-2-phenyl-m-dioxane, about 1500 ml of ethanol, about 500 ml of water and about 20 ml of sulfuric acid was refluxed for about 2 hours. The ethanol was removed, the acid neutralized with solid bicarbonate, the mixture steam distilled to remove benzaldehyde and then saturated with potassium carbonate. This mixture was extracted three times with ether. The ether extracts were combined, dried and evaporated. Toluene was added and evaporated. The residue was distilled via a Kugelrohr (about 0.1 mm, 170° C.) giving an oil. This oil was dissolved in about 300 ml of toluene, cooled and diluted with two volumes of petroleum ether. Refrigeration produced about 184.69 g of the desired title compound as a solid.

EXAMPLE 27

3-(Hexadecyloxy)-2-(benzyloxy)-1-propanol

To a suspension of about 14.26 g of washed about 50% sodium hydride in about 500 ml of dimethylformamide was added about 49.2 g of 2-(benzyloxy)-1,3-propanediol over about 20 minutes. The mixture was stirred for about 40 minutes, then cooled to about 0° C. and about 95.13 g of hexadecyl iodide were added. After standing about 10 minutes, the mixture was stirred at room temperature for about 3 hours, then filtered through celite and diluted with about 1000 ml of water. This mixture was extracted with petroleum ether. The ether extract was dried and the solvent removed giving an oil. This oil was chromatographed on a column of florisil, eluting first with petroleum ether and then successively with about 5% and about 10% ether in petroleum ether to elute the product, giving about 28.8 g of the desired title compound as a light yellow oil.

EXAMPLE 28

2-(Benzyloxy)-3-(octadecyloxy)-1-propanol

To a suspension of about 26.07 g of washed about 50% sodium hydride in about 1000 ml of dimethylformamide was added about 90 g of 2-(benzyloxy)-1,3-propanediol with stirring under argon. An about 187.88 g portion of octadecyl iodide and about 150 ml of tetrahydrofuran were added and the thick mixture was stirred with a glass rod, and then with magnetic stirring for about 3 hours. Water was then added and the mixture was extracted with ether. The ether extract was washed with brine, dried and filtered through a pad of florisil. The solvent was removed and the residue chromatographed on florisil, eluting first with petroleum ether, then with about 10% ether in petroleum ether and finally eluting the product with about 30% ether in petroleum ether, giving about 73.3 g of the desired title compound as a waxy solid.

By following the methods outlined above in Examples 27 and 28, 2-(benzyloxy)-1,3-propanediol is alkylated with the indicated alkyl iodides to provide the 1-propanol derivatives listed in Table III below.

TABLE III

| 1-Propanol Derivative | Alkyl Iodide |
| --- | --- |
| 2-(benzyloxy)-3-(nonadecyloxy)-1-propanol | nonadecyl iodide |
| 2-(benzyloxy)-3-(heptadecyloxy)-1-propanol | heptadecyl iodide |
| 2-(benzyloxy)-3-(pentadecyloxy)-1-propanol | pentadecyl iodide |
| 2-(benzyloxy)-3-(tetradecyloxy)-1-propanol | tetradecyl iodide |
| 2-(benzyloxy)-3-(tridecyloxy)-1-propanol | tridecyl iodide |
| 2-(benzyloxy)-3-(2-methylhexadecyloxy)-1-propanol | 2-methylhexadecyl iodide |
| 2-(benzyloxy)-3-(3-ethylpentadecyloxy)-1-propanol | 3-ethylpentadecyl iodide |
| 2-(benzyloxy)-3-(2,4-dimethylhexadecyloxy)-1-propanol | 2,4-dimethylhexadecyl iodide |

TABLE IV

| Alkyl Amines |
| --- |
| trimethyl amine |
| dimethyl amine |
| methyl amine |
| triethyl amine |
| diethyl amine |
| ethyl amine |
| tripropyl amine |
| dipropyl amine |
| propyl amine |
| pyrrolidine |
| N—methyl pyrrolidine |
| butyl amine |
| ammonia |

What is claimed is:

1. 7-(Acetyloxy)-4-hydroxy-N,N,N,8-tetramethyl-3,5,9-trioxa-4-phosphapentacosan-1-aminium, 4-oxide, hydroxide, inner salt.

2. 7-(Acetyloxy)-4-hydroxy-N,N,N,6-tetramethyl-3,5,9-trioxa-4-phosphapentacosan-1-aminium, 4-oxide, hydroxide, inner salt.

3. 7-(Acetyloxy)-4-hydroxy-N,N,N,8,8-pentamethyl-3,5,9-trioxa-4-phosphapentacosan-1-aminium, 4-oxide, hydroxide, inner salt.

4. A pharmaceutical composition of matter in dosage unit form comprising 7-(acetyloxy)-4-hydroxy-N,N,N,6-tetramethyl-3,5,9-trioxa-4-phosphapentacosan-1-aminium, 4-oxide, hydroxide, inner salt.

* * * * *